United States Patent
Shim et al.

(10) Patent No.: US 8,538,546 B2
(45) Date of Patent: Sep. 17, 2013

(54) DEVICE FOR GENERATING A SIGNAL

(75) Inventors: Han Bo Shim, Seongnam-si (KR); Won Woo Cho, Yongin-si (KR); Jung Jin Hwang, Daejeon (KR); Kwang Seop Kim, Daejeon (KR); Young Dae Seo, Daejeon (KR); Han Jung, Daejeon (KR); Byung Hyuk Kim, Daejeon (KR); Yong Un Kim, Daejeon (KR)

(73) Assignee: Intromedic Co., Ltd, Seoul (KR)

( * ) Notice: Subject to any disclaimer, the term of this patent is extended or adjusted under 35 U.S.C. 154(b) by 0 days.

(21) Appl. No.: 13/416,941

(22) Filed: Mar. 9, 2012

(65) Prior Publication Data

US 2012/0200318 A1    Aug. 9, 2012

Related U.S. Application Data

(63) Continuation of application No. 12/298,880, filed as application No. PCT/KR2007/002047 on Apr. 26, 2007, now Pat. No. 8,185,211.

(30) Foreign Application Priority Data

Apr. 28, 2006   (KR) .................. 10-2006-0038953

(51) Int. Cl.
     *A61N 1/08*    (2006.01)
(52) U.S. Cl.
     USPC ................................ 607/60; 607/2
(58) Field of Classification Search
     USPC .......................... 607/33, 40, 60, 61
     See application file for complete search history.

(56) References Cited

U.S. PATENT DOCUMENTS

| | | | |
|---|---|---|---|
| 5,522,865 A | 6/1996 | Schulman et al. |
| 7,444,184 B2 | 10/2008 | Boveja et al. |
| 7,959,560 B2 | 6/2011 | Mori et al. |
| 2002/0165622 A1 | 11/2002 | Fujii |
| 2005/0029124 A1 | 2/2005 | Holmes et al. |
| 2006/0050536 A1 | 3/2006 | Kim et al. |
| 2006/0241578 A1 | 10/2006 | Honda |

FOREIGN PATENT DOCUMENTS

| | | |
|---|---|---|
| FR | 2 612 712 A1 | 9/1988 |
| JP | 2003-325440 A | 11/2003 |
| JP | 2006-026059 A | 2/2006 |
| KR | 10-2006-0070574 A | 6/2006 |

OTHER PUBLICATIONS

International Search Report and Written Opinion dated Aug. 8, 2007 as received in application No. PCT/KR2007/002047.

*Primary Examiner* — Brian T Gedeon
(74) *Attorney, Agent, or Firm* — Maschoff Brennan

(57) ABSTRACT

The present invention relates to a device for generating a signal and method for controlling operation of the same. The present invention provides a device for generating a signal, which includes an electrode, if connected to an external power source, supplied with a voltage from the external power source, a signal generating unit having a plurality of terminals, the signal generating unit deciding whether to operate the device according to a size of a voltage applied to a first terminal among a plurality of the terminals, the signal generating unit outputting a prescribed signal according to the decision, and a control circuit, if the electrode is connected to a plurality of the terminals, controlling a voltage applied to a plurality of the terminals. Accordingly, the present invention is able to control whether to operate a signal generating device using an external power source.

19 Claims, 7 Drawing Sheets

DEVICE FOR GENERATING A SIGNAL

RELATED APPLICATIONS

This application is a Continuation of U.S. application Ser. No. 12/298,880, now U.S. Pat. No. 8,185,211, filed Oct. 28, 2008 which is a 35 U.S.C. §371 national phase application of PCT/KR2007/002047 (WO 2007/126247) filed on Apr. 26, 2007, and claims the priority benefit of Korean Patent Application No. 10-2006-0038953 filed in Korea on Apr. 28, 2006. The entire disclosure of each of these priority applications is hereby incorporated herein by reference.

TECHNICAL FIELD

The present invention relates to a device for generating a signal and method for controlling operation of the same.

BACKGROUND ART

First of all, a method of controlling an operation of a device according to a related art is explained as follows.

According to a related art, a reed switch is used to control an operation of a device.

The reed switch is a sort of a magnetic switch including a pair of reeds, which are ferromagnetic and elastic substance to be well attracted to a magnet, put in a small glass tube charged with inert gas to prevent corrosion of the reeds.

The operational control using the reed switch includes the following steps.

First of all, a magnet is placed in the vicinity of the reed switch. If the magnet is located at a central part of the reed switch, induction line of the magnet is formed from a north pole to a south pole. In this case, the induction line passing through the reeds magnetizes tips of the reeds into the north and south poles, respectively. So, an attractive force is generated between the reeds to make them come into contact with each other, whereby the device is turned on.

Meanwhile, if the magnet is placed distant from the reed switch, the magnetized reeds return to their original states to be separated from each other. So, the device is turned off.

However, in the above-explained related art, since additional current is consumed for the operational control by the reed switch, a life span of an internal battery is reduced.

DISCLOSURE OF THE INVENTION

An object of the present invention is to provide a device for generating a signal and method for controlling operation of the same, by which an operation can be controlled using a control circuit including small-size passive devices.

Another object of the present invention is to provide a device for generating a signal and method for controlling operation of the same, by which internal power consumption can be minimized by controlling an operation using an external power source.

Another object of the present invention is to provide a device for generating a signal and method for controlling operation of the same, by which a presence or non-presence of an operation can be decided according to a size of a voltage applied by an external power source.

To achieve these and other advantages and in accordance with the purpose of the present invention, as embodied and broadly described, a device for generating a signal according to the present invention includes an electrode, if connected to an external power source, supplied with a voltage from the external power source, a signal generating unit having a plurality of terminals, the signal generating unit deciding whether to operate the device according to a size of a voltage applied to a first terminal among a plurality of the terminals, the signal generating unit outputting a prescribed signal according to the decision, and a control circuit, if the electrode is connected to a plurality of the terminals, controlling a voltage applied to a plurality of the terminals.

To further achieve these and other advantages and in accordance with the purpose of the present invention, a method of controlling an operation of a signal generating device according to the present invention includes a step (a) of if an external power source is connected, receiving a voltage from the external power source, a step (b) of if the voltage is received from the external power source, applying a voltage to a prescribed terminal provided to the signal generating device, and a step (C) of deciding whether to operate the signal generating device according to a size of the voltage applied to the prescribed terminal.

Accordingly, the present invention is able to control a presence or non-presence of an operation of a signal generating device using an external power source.

DESCRIPTION OF MAJOR PARTS OF DRAWINGS

100: Signal Generating Device
110: Electrode

120: Control Circuit
130: Signal Generating Unit
140: Power Source Unit
200: External Power Source
132: First Terminal
134: Second Terminal

BEST MODE FOR CARRYING OUT THE INVENTION

Reference will now be made in detail to the preferred embodiments of the present invention, examples of which are illustrated in the accompanying drawings.

A configuration of a signal generating device 100 according to the present invention is explained in detail with reference to FIG. 1, FIG. 2A and FIG. 2B as follows.

Figure 1:
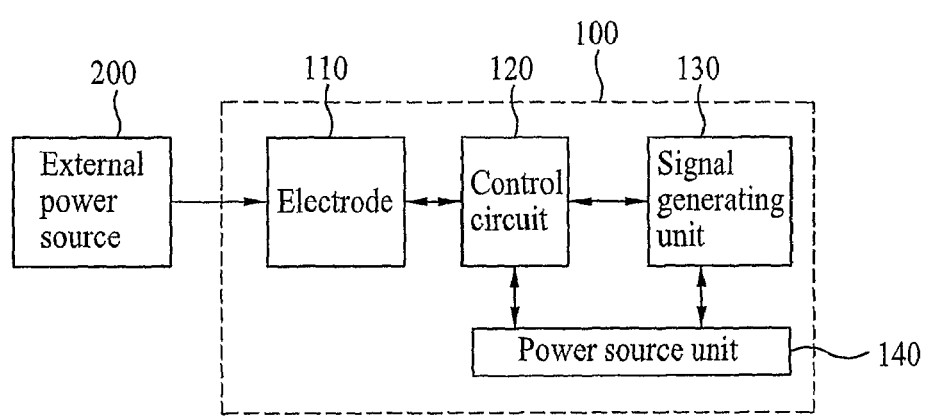
FIG. 1 is a block diagram of a device for generating a signal according to one embodiment of the present invention.

Referring to FIG. 1, the signal generating device 100 includes an electrode 110, a control circuit 120, a signal generating unit 130, and a power source unit 140.

The signal generating device 100 can be a capsule type medical device. In this case, the signal generating device 100 is configured as shown in FIG. 2A or FIG. 2B.

Figure 2A:
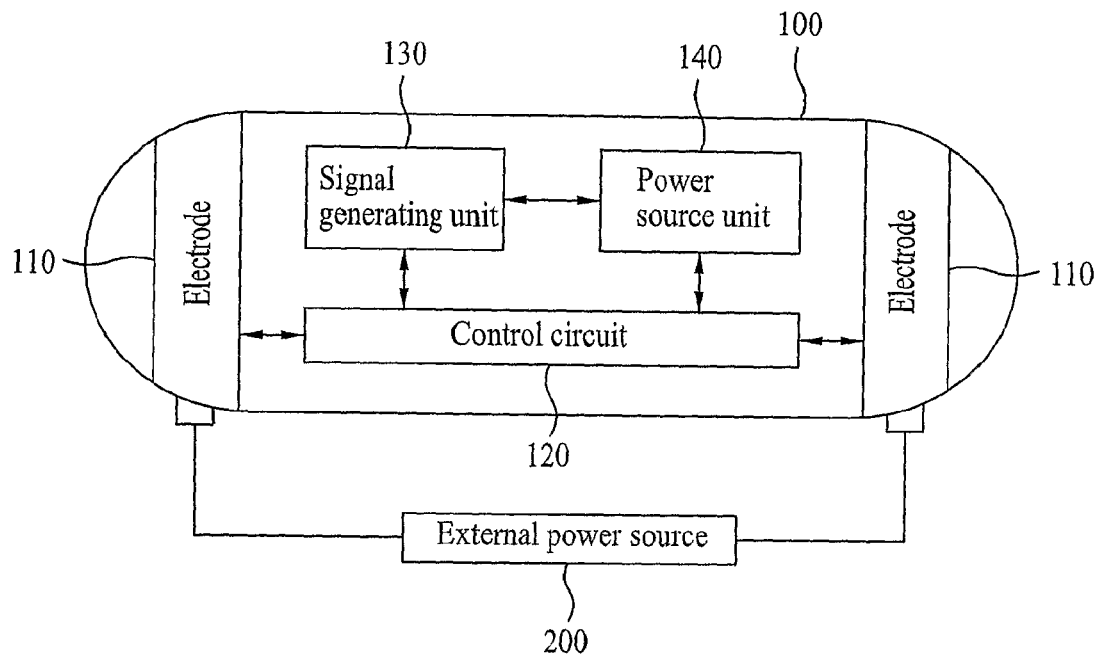
FIG. 2A is a diagram of a signal generating device having an external power source connected thereto according to one embodiment of the present invention.

Yet, FIG. 2A shows a case that an external power source 200 is connected to the electrode 110. FIG. 2B shows a case that the external power source 200 is disconnected from the electrode 110.

As the electrode 110 is connected to the external power source 200, a voltage is applied to the electrode 110 by the external power source 200.

As the electrode 110 is disconnected from the connected external power source 200, a signal generated by the signal generating unit 130 is externally outputted.

At least two electrodes 110 are provided. In the following description, pair of the electrodes 110 are provided for example.

If the electrodes 110 are connected to the external power source 200, one of the two electrodes 110 is connected to a cathode (−) of the external power source 220 and the other is connected to an anode (+) of the external power source 200.

If the external power source 220 is disconnected from the electrodes 110, one of the two electrodes externally outputs a signal generated by the signal generating unit 130 and the other outputs a ground signal generated by the signal generating unit 130.

And, the electrodes 110 are provided to a portion of a periphery of the signal generating device 100.

In case that the signal generating device 100 is configured with a capsule type periphery, the electrodes 110, as shown in FIG. 5A, FIG. 5B, FIG. 5C, and FIG. 5D, can provided to the portion of the periphery of the signal generating device 100 in various shapes.

The signal generating unit 130 includes a plurality of terminals. The signal generating unit 130 decides a presence or non-presence of an operation of the signal generating device 100 in correspondence to a size of a voltage applied to a first one of a plurality of the terminals and then outputs a prescribed signal according to the corresponding decision.

The first terminal receives either a voltage over a reference voltage or a voltage below the reference voltage according to a presence or non-presence of a voltage application by the external power source 200. The reference voltage is the voltage as a reference for deciding the presence or non-presence of operation of the signal generating device 100. And, the reference voltage is used to decide the presence or non-presence of the operation of the signal generating device 100 by comparing the size of the voltage applied to the first terminal to the reference voltage. In this case, the reference voltage is set in advance for the signal generating device 100.

For instance, if the electrode 110 is connected to the external power source 200, the first terminal receives the voltage over the reference voltage according to the voltage application by the external power source 200. So, as the voltage over the reference voltage is applied to the first terminal, the signal generating unit 130 decides not to operate the signal generating device 100 and then does not output any signal.

Meanwhile, in case that the external power source 200 is disconnected from the electrode 110, the first terminal receives the voltage below the reference voltage. So, as the voltage below the reference voltage is applied to the first terminal, the signal generating unit 130 decides to operate the signal generating device 100 and then generated to output a prescribed signal.

The control circuit 120 controls a voltage applied to a plurality of the terminals as the electrode 110 is connected to a plurality of the terminals.

The control circuit 120 includes prescribed passive devices. And, the control circuit 120 plays a role as a switch in deciding the presence or non-presence of the signal generating device 100 by controlling the voltage applied to the terminals.

For instance, the control unit 120, according to the voltage application by the external power source 200, controls the first terminal to receive the voltage over the reference voltage.

Meanwhile, if the external power source 200 is disconnected, the control circuit 120 receives a prescribed signal outputted by the signal generating unit 130 and then controls the received signal to be outputted via the electrode 110.

The power source unit 140 supplies a power required for the operation of the signal generating device 100.

For instance, if it is decided to operate the signal generating device 100, the power source unit 140 supplies the power required for the operation of the signal generating device 100.

On the other hand, if it is decided not to operate the signal generating device 100, the power source unit 140 does not supply a power required for the operation except a minimum power required for maintaining an internal switch status.

Figure 6:
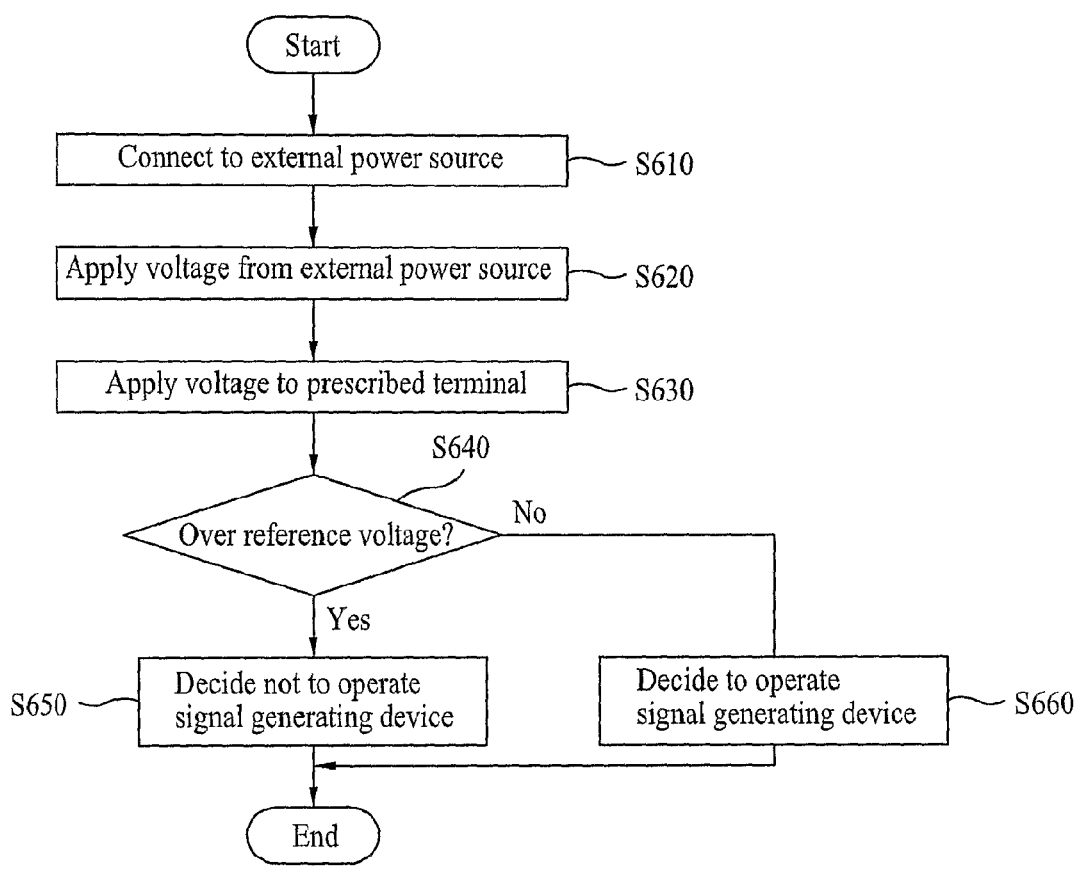
FIG. 6 is a flowchart of a method of controlling an operation of a signal generating device according to one embodiment of the present invention.

A method of controlling an operation of a signal generating device 100 according to the present invention is explained in detail with reference to FIG. 3A and FIG. 6 as follows.

Figure 3A:
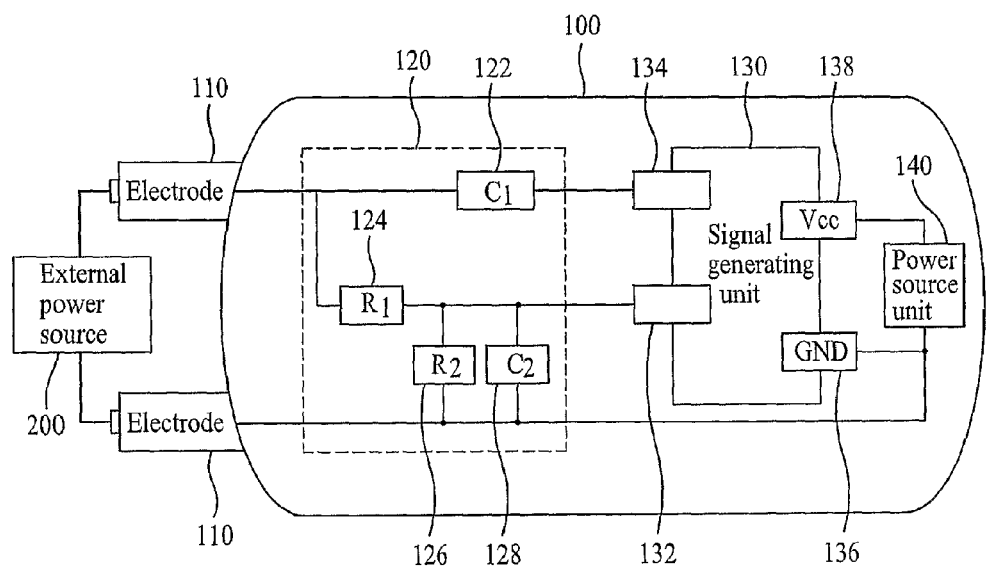
FIG. 3A is a diagram of an internal configuration of a signal generating device having an external power source connected thereto according to one embodiment of the present invention.

Referring to FIG. 3A, the signal generating device 100 includes an electrode 110 connected to an external power source 200, a control circuit 120 including a plurality of passive devices 122, 124, 126, and 128, a signal generating unit 130 including a plurality of terminals 132, 134, 136, and 138, and a power source unit 140 supplying a power to the signal generating device 100.

In particular, the control circuit 120 includes a first capacitor 122, a first resistor 124, a second resistor 126, and a second capacitor 128.

And, the signal generating unit 130 includes a first terminal 132 receiving a voltage required for deciding a presence or non-presence of an operation of the signal generating device 100 and a second terminal 134 outputting a signal generated from the operation of the signal generating device 100. Moreover, the signal generating unit 130 further includes the terminals 136 and 138 connected to the power source unit 140.

The electrode 110 is connected to an external power source 200 (S610).

For instance, in case that the signal generating device 100 is provided with two electrodes 110, one of the two electrodes is connected to a cathode (−) of the external power source 200 and the other is connected to an anode (+).

For instance, if the external power source 200 includes a connecting member provide to its periphery to be connected to the signal generating device 100, the signal generating device 100 is connected to the external power source 200 by the connecting member. In particular, as the electrode 110 is provided to a part connected with the connecting member, the electrode can be connected to the external power source 200.

The electrode 110 receives a prescribed voltage from the connected external power source 200 (S620).

For instance, in case that the external power source 200 has a voltage of 3V, the electrode 110 can be supplied with the voltage of 3V by the external power source 200.

In case that the external power source 200 is a DC power source, the electrode 110 is supplied with a DC voltage by the external power source 200.

And, the first terminal 132 is supplied with a voltage of a predetermined size by the control circuit 120.

By taking a case that the external power source 200 is a DC power source as an example, a case of applying a voltage of a predetermined size to the first terminal 132 is explained as follows.

First of all, the control circuit 120 is constructed with passive devices including a first capacitor 122, a first resistor 124, a second resistor 126, and a second capacitor 128.

As a DC voltage is supplied by the external power source 200, each of the first and second capacitors 122 and 128 works as open, the control circuit 120 substantially includes the first resistor 124 and the second resistor 126 only.

In the configuration of the control circuit 120, since the first resistor 124 is configured to have a size considerably smaller than that of the second resistor 126, a voltage is mainly applied to the second resistor 126 due to the voltage divider rule.

So, the first terminal 132 connected to parallel with the second resistor 126 is supplied with a voltage of the same size of the voltage applied to the second resistor 126.

For instance, if a voltage supplied by the external power source 200 is 3V, if the first resistor 124 has 0.5 M0, and if the second resistor 126 has 10 MQ, the first terminal 132 can be supplied with a voltage of 20/7V, i.e., about 2.86V according to the voltage divider rule.

Preferably, the control circuit 120 is designed to apply a voltage over a reference voltage to the first terminal 132 by a voltage application of the external power source 200.

For instance, if a voltage applied by the external power source 200 is 3V and if the reference voltage is 1.5V, the control circuit 120 can be designed by adjusting resistances of the first and second resistors 124 and 126 to enable a voltage applied to the second resistor 126 to exceed 1.5V.

Namely, based on the voltage divider rule, by adjusting the second resistor 124 to be equal to the first resistor 12 at least, it is able to apply a voltage over the reference voltage of 1.5V to the first terminal 132.

Subsequently, the signal generating unit 130 decides whether the voltage applied to the first terminal 132 is equal to or greater than the reference voltage (S640).

As mentioned in the foregoing description, if the control circuit 120 is designed to enable the first terminal 132 to be supplied with the voltage over the reference voltage, the signal generating unit 130 decides that the voltage over the reference voltage is applied to the first terminal 132.

On the other hand, if the control circuit 120 is designed to enable the first terminal 132 not to be supplied with the voltage over the reference voltage, the signal generating unit 130 can decide that the voltage over the reference voltage is not applied to the first terminal 132.

As a result of the decision, if it is decided that the voltage over the reference voltage is applied to the first terminal 132, the signal generating unit 130 decides not to operate the signal generating device 100 (S650).

As a result of the decision, if it is decided that the voltage over the reference voltage is not applied to the first terminal 132, the signal generating unit 130 decides to operate the signal generating device 100 (S660).

The signal generating unit 130 is provided with a switching circuit internally including a control pin operative according to whether the voltage applied to the first terminal 132 is over the reference voltage.

So, the signal generating unit 130 is able to decide whether to operate the signal generating device 100 in correspondence to an operation of the control pin based on whether the voltage applied to the first terminal 132 is over the reference voltage.

Figure 7:
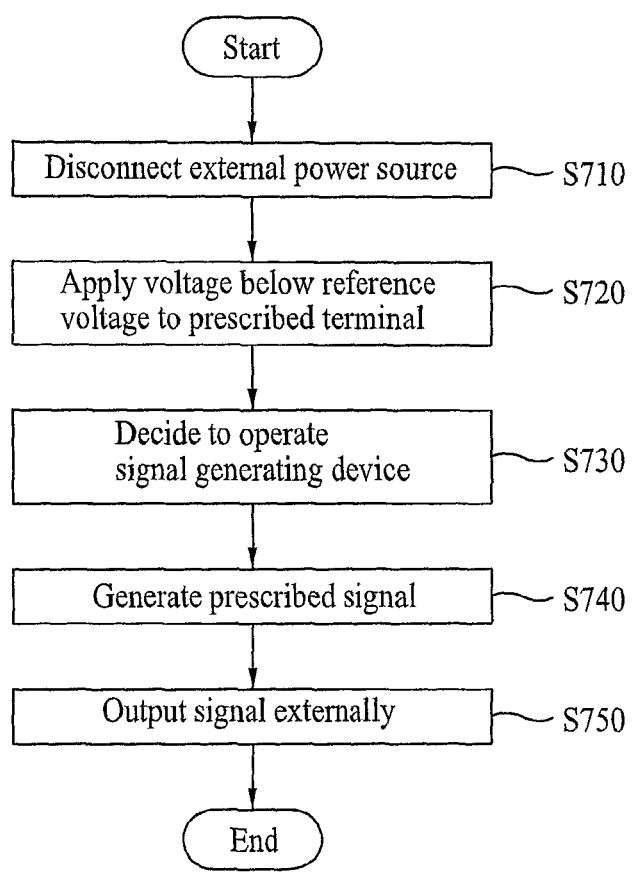
FIG. 7 is a flowchart of a method of controlling an operation of a signal generating device according to another embodiment of the present invention.

A method of controlling an operation of a signal generating device 100 according to the present invention is explained in detail with reference to FIG. 3B and FIG. 7 as follows.

Figure 3B:
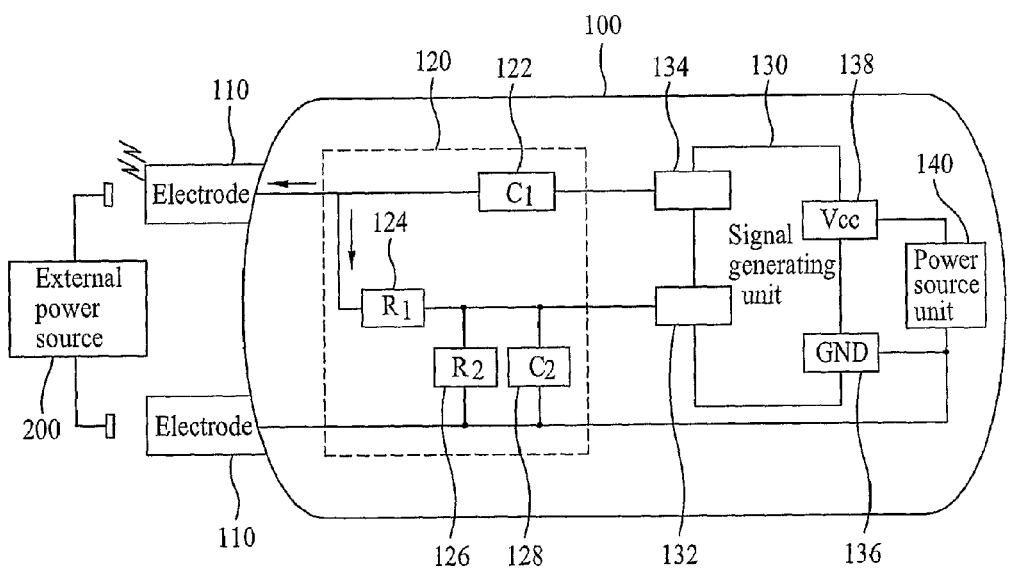
FIG. 3B is a diagram of an internal configuration of a signal generating device having an external power source disconnected therefrom according to one embodiment of the present invention.

Referring to FIG. 3B, the signal generating device 100 has the same configuration of the former signal generating device 100 shown in FIG. 3A. Yet, FIG. 3B shows the signal generating device 100 from which the external power source 200 is disconnected, whereas FIG. 3A shows the signal generating device 100 to which the external power source 200 is connected. Subsequently, the connected external power source 200 is disconnected from the electrode 100.

For instance, in case that the signal generating device 100 is connected by a connecting member provided to the external power source 200, it is able to remove the external power source 200 by separating the external power source 200 from the signal generating device 100.

As the external power source 200 is disconnected, a first terminal 132 is supplied with a voltage below a reference voltage (S720).

As the external power source 200 is disconnected, one end of the second resistor 126 is grounded as soon as a voltage of OV is applied to the second resistor 126. And, the first terminal 132 connected in parallel with the second resistor 126 is supplied with a voltage of OV. So, the first terminal 132 can be supplied with the voltage below the reference voltage.

Subsequently, the signal generating unit 130 decides to operate the signal generating device 100 as the voltage below the reference voltage is applied to the first terminal 132 (S730).

The signal generating unit 130 is provided with a switching circuit internally including a control pin operative according to whether the voltage applied to the first terminal 132 is over the reference voltage.

So, the signal generating unit 130 is able to decide whether to operate the signal generating device 100 in correspondence to an operation of the control pin based on the voltage, which is applied to the first terminal 132, below the reference voltage.

The signal generating unit 130 generates a prescribed signal according to the decision (S740).

The signal generating unit 130 generates an AC signal having a characteristic over a reference frequency.

The generated signal is inputted to the electrode 110 via the control circuit 120.

The electrode 110 outputs the inputted signal externally (S750).

In designing the control circuit 120, since a first capacitor 122 is designed to have a considerably small impedance value over the reference frequency, the signal is externally outputted via the electrode 110 by being barely affected by the first capacitor 122.

Meanwhile, most of the signal is externally outputted via the electrode 110. Yet, a small quantity of the signal can be internally introduced.

Yet, in designing the control circuit 120, since an impedance value of the second capacitor 128 is designed to have a value considerably smaller than that of the second resistor 126 connected in parallel, it can be assumed that the second resistor 126 plays a role as an infinite resistance. And, the impedance value of the first resistor 124 is adjusted to be considerably greater than that of the second capacitor 128. So, compared to the impedance value by the first resistor 124, the impedance value of the second capacitor 128 can be assumed to have almost zero.

So, the internally introduced signal is mostly interrupted by the first resistor 124, thereby affecting the first terminal 132 barely. Hence, the first terminal 132 is able to keep maintaining the voltage below the reference voltage.

An internal configuration of a signal generating device 400 having an external power source disconnected therefrom according to the present invention is explained in detail with reference to FIG. 4 as follows.

Figure 4:
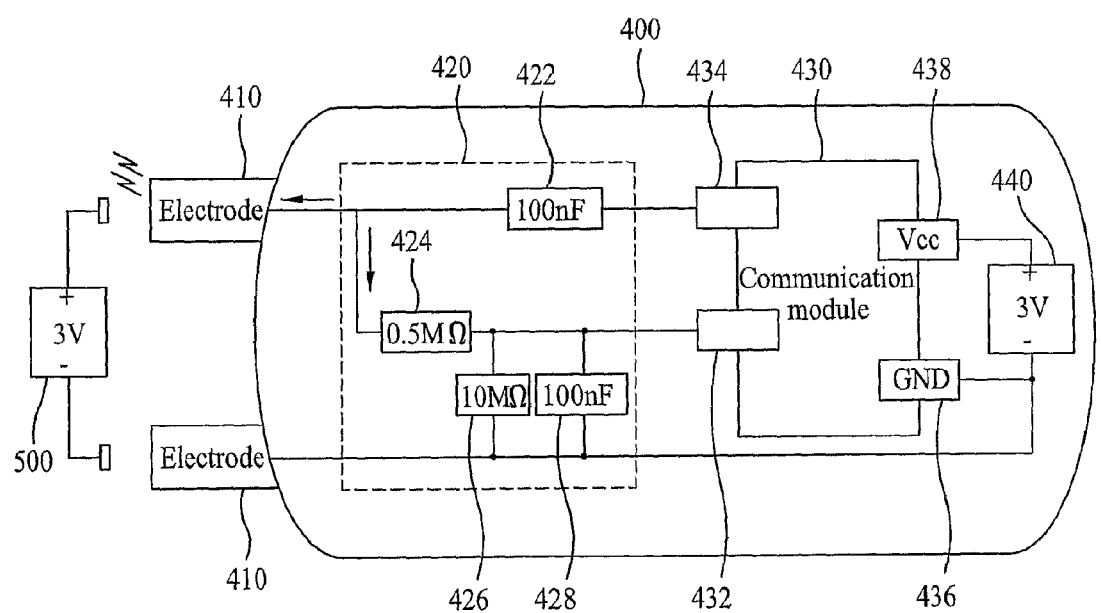
FIG. 4 is a diagram of an internal configuration of a signal generating device having an external power source disconnected therefrom according to another embodiment of the present invention.
Figure 5A:
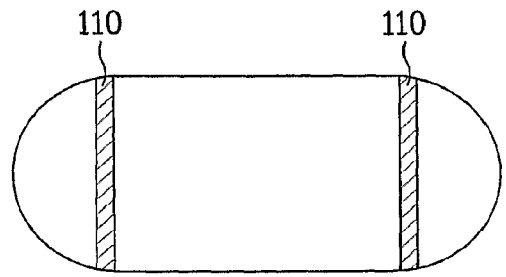
FIG. 5A is a diagram of an electrode provided to a periphery of a signal generating device according to a first embodiment of the present invention.
Figure 5B:
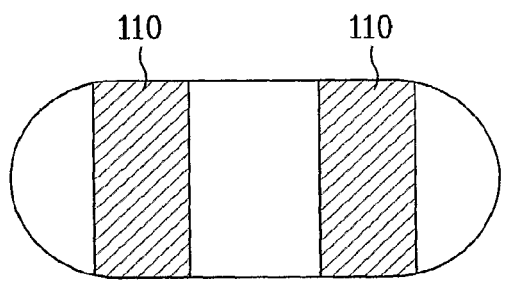
FIG. 5B is a diagram of an electrode provided to a periphery of a signal generating device according to a second embodiment of the present invention.
Figure 5C:
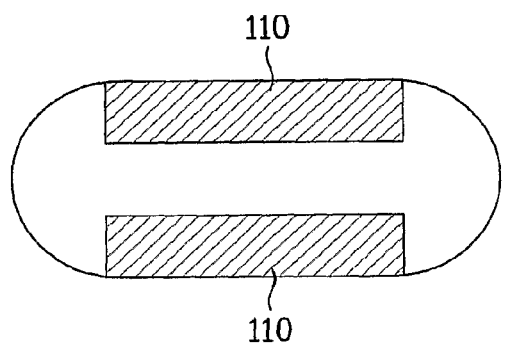
FIG. 5C is a diagram of an electrode provided to a periphery of a signal generating device according to a third embodiment of the present invention.
Figure 5D:
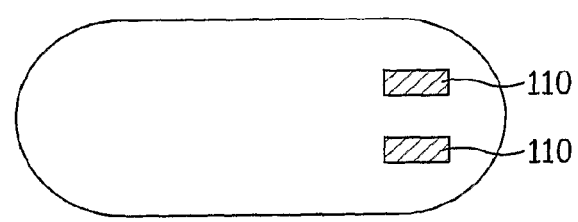
FIG. 5D is a diagram of an electrode provided to a periphery of a signal generating device according to a fourth embodiment of the present invention.

FIG. 4 is a diagram to explain a configuration and operation of the signal generating device 400 from which an external power source 500 is disconnected.

Referring to FIG. 4, the signal generating device 400 includes an electrode 410, a control circuit 420, a communication module 430, and a power source unit 440.

Figure 2B:
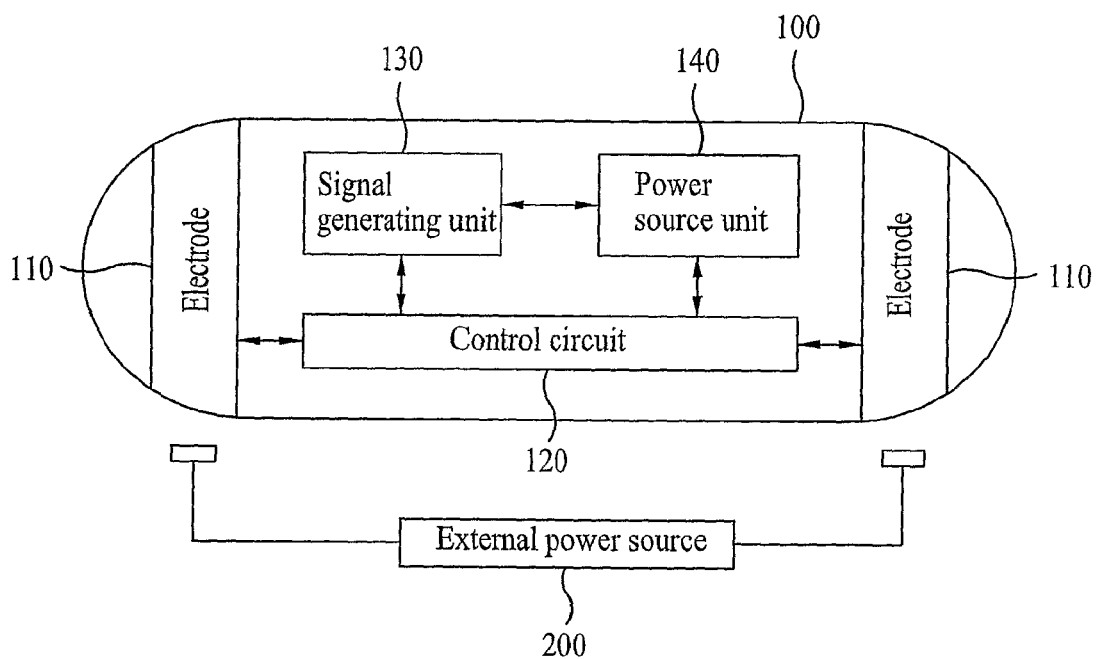
FIG. 2B is a diagram of a signal generating device having an external power source disconnected therefrom according to one embodiment of the present invention.

It is assumed that the electrode 410 has the same function and operation of the former electrode 110 shown in FIG. 2A or FIG. 2B.

The control circuit 420 is equivalent to the former control circuit 120 shown in FIG. 2A or FIG. 2B but includes resistors and capacitors having specific values.

The control circuit 420 includes a first capacitor 422 having 100 nF, a first resistor 424 having 0.5 MQ, a second resistor 426 having 10 MD, and a second capacitor 428 having 100 nF.

In this case, an impedance value of each of the passive devices provided to the control circuit 420 should meet a predetermined condition.

For instance, according to the condition, an impedance value attributed to the first and second capacitors 422 and 428 should be adjusted to have a value considerably smaller than an impedance value attributed to the first and second resistors 424 and 426. And, an impedance value attributed to the first resistor 424 should be adjusted to have a value considerably smaller than an impedance value attributed to the second resistor 426.

The communication module 430 corresponds to the signal generating unit 130 shown in FIG. 2A or FIG. 2B but is provided as one embodiment of a signal generating unit.

The power unit 440 corresponds to the former power unit 140 shown in FIG. 2A or FIG. 2B but has a voltage value of 3V specifically.

As the external power source 500 is disconnected, one end of the second resistor 426 is grounded as soon as a voltage of OV is applied to the second resistor 426. So, the first terminal 432 connected in parallel with the second resistor 426 is supplied with a voltage of OV as a voltage below a reference voltage.

The communication module 430 decides to operate the signal generating device 400 based on the voltage of OV applied to the first terminal 432 and then generated an AC signal having a characteristic over a reference frequency.

Since the first capacitor 422 is designed to have a very small impedance value over the reference frequency, the signal is externally outputted via the electrode 410 without being barely affected by the first capacitor 422.

Meanwhile, most of the signal is externally outputted via the electrode 410. Yet, a small quantity of the signal can be internally introduced.

Yet, in designing the control circuit 420, since an impedance value of the second capacitor 128 is designed to have a value considerably smaller than that of the second resistor 426 connected in parallel, it can be assumed that the second resistor 426 plays a role as an infinite resistance. And, the impedance value of the first resistor 424 is adjusted to be considerably greater than that of the second capacitor 428. So, the impedance value of the second capacitor 428 can be assumed to have almost zero.

So, the internally introduced signal is mostly interrupted by the first resistor 424, thereby affecting the first terminal 432 barely. Hence, the first terminal 432 is able to keep maintaining the voltage below the reference voltage.

While the present invention has been described and illustrated herein with reference to the preferred embodiments thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

Industrial Applicability

Accordingly, the present invention is able to perform an operation control using a control circuit including small-sized passive devices. Hence, it is unnecessary to increase a volume of a device to be provided with an operation control circuit.

According to the present invention, it is able to decide whether to operate a device using an external power source. Hence, an operation of the device can be conveniently controlled.

According to the present invention, it is able to control an operation of a device using an external power source. Hence, it is able to minimize consumption of an internal power source.

The invention claimed is:

1. A device for generating a prescribed signal, comprising:
   an electrode configured to be supplied with a first voltage from an external power source, the external power source being outside the device, when the device is connected to the external power source;
   a signal generating unit having a plurality of terminals, the plurality of terminals including a first terminal, wherein the signal generating unit is configured
   to decide whether to operate the device according to a size of a second voltage applied to the first terminal, and
   to output a prescribed signal, the prescribed signal being an AC signal having a frequency over a reference frequency, according to the decision; and
   a control circuit configured to control the second voltage, to output the controlled second voltage to the first terminal, and to control the prescribed signal to be outputted via the electrode, according as whether the first voltage is supplied via the electrode from the external power source.

2. The device of claim 1, wherein the device is a capsule type medical device.

3. The device of claim 1, wherein the electrode is disposed in an edge of the device.

4. The device of claim 1, wherein the electrode comprises at least two first and second electrodes.

5. The device of claim 4, wherein the control circuit comprises:
   a first resistor having one side connected to the first electrode;

a second resistor connected between the other side of the first resistor and the second electrode;

a first capacitor connected between the first electrode and a second terminal of the signal generating unit, the plurality of terminals including the second terminal through which the prescribed signal is outputted to the control circuit; and a second capacitor connected in parallel with the second resistor.

6. The device of claim 5, wherein the first resistor has a size smaller than that of the second resistor.

7. The device of claim 5, wherein the first resistor has a size equal to that of the second resistor.

8. The device of claim 1, wherein the signal generating device decides not to operate the device if the first voltage is supplied from the external power source.

9. The device of claim 1, wherein the signal generating device decides to operate the device if the first voltage is not supplied from the external power source.

10. The device of claim 1, further comprising a power source unit configured to supply a power required for the operation of the signal generating device.

11. The device of claim 1, wherein the size of the second voltage differs from a size of the first voltage.

12. The device of claim 1, wherein the signal generating unit is configured to output the prescribed signal via a second terminal according to the decision, the plurality of the terminals including the second terminal.

13. The device of claim 12, wherein the control circuit outputs the prescribed signal received from the signal generating unit to outside of the device via the electrode.

14. The device of claim 1, wherein the control circuit is configured
   to generate either the second voltage over a reference voltage or the second voltage below the reference voltage, according as whether the first voltage is supplied from the external power source, and
   to output the generated second voltage to the first terminal.

15. The device of claim 14, wherein the control circuit is configured to control the first terminal to be supplied with the second voltage over the reference voltage if the first voltage is supplied from the external power source via the electrode.

16. The device of claim 14, wherein the control circuit is configured to control the first terminal to be supplied with the second voltage below the reference voltage if the first voltage is not supplied from the external power source via the electrode.

17. The device of claim 14, wherein the signal generating unit is configured to decide whether to operate the device according as whether the second voltage over the reference voltage is applied to the first terminal.

18. The device of claim 17, wherein the signal generating device decides not to operate the device and does not output the prescribed signal, if the second voltage over the reference voltage is applied to the first terminal.

19. The device of claim 17, the signal generating device decides to operate the device and outputs the prescribed signal, if the second voltage below the reference voltage is applied to the first terminal.

* * * * *